(12) United States Patent
Ullberg

(10) Patent No.: US 6,940,942 B2
(45) Date of Patent: Sep. 6, 2005

(54) SCANNING-BASED DETECTION OF IONIZING RADIATION FOR TOMOSYNTHESIS

(75) Inventor: Christer Ullberg, Sollentuna (SE)

(73) Assignee: XCounter AB, Danderyd (SE)

( * ) Notice: Subject to any disclaimer, the term of this patent is extended or adjusted under 35 U.S.C. 154(b) by 0 days.

(21) Appl. No.: 10/657,241

(22) Filed: Sep. 9, 2003

(65) Prior Publication Data

US 2005/0008124 A1 Jan. 13, 2005

(30) Foreign Application Priority Data

Jul. 8, 2003 (SE) .............................................. 0302022

(51) Int. Cl.⁷ ................................................ G21K 1/12
(52) U.S. Cl. ........................... 378/26; 378/22; 378/197
(58) Field of Search ........................... 378/4, 19, 8, 23, 378/21, 20, 26, 37, 98.8, 147, 22

(56) References Cited

U.S. PATENT DOCUMENTS

| | | | |
|---|---|---|---|
| 4,064,440 A | * | 12/1977 | Roder .......................... 378/57 |
| 4,466,113 A | | 8/1984 | Strecker |
| 4,953,189 A | * | 8/1990 | Wang .......................... 378/108 |
| 5,022,060 A | | 6/1991 | Trotel |
| 5,126,938 A | | 6/1992 | Oda |
| 5,511,106 A | * | 4/1996 | Doebert et al. ............. 378/146 |
| 6,118,125 A | | 9/2000 | Carlson et al. |
| 6,118,841 A | | 9/2000 | Lia |
| 6,243,438 B1 | | 6/2001 | Nahaliel et al. |
| 6,337,482 B1 | | 1/2002 | Francke |
| 6,373,065 B1 | | 4/2002 | Francke et al. |
| 6,385,282 B1 | | 5/2002 | Francke et al. |
| 6,414,317 B1 | | 7/2002 | Francke et al. |
| 6,474,397 B1 | | 11/2002 | Gunkel et al. |
| 6,477,223 B1 | | 11/2002 | Francke |
| 6,518,578 B1 | | 2/2003 | Francke et al. |
| 6,522,722 B1 | | 2/2003 | Francke |
| 6,546,070 B1 | | 4/2003 | Francke |
| 6,628,745 B1 | | 9/2003 | Annis et al. |
| 2003/0072419 A1 | * | 4/2003 | Bruder et al. ............... 378/210 |

FOREIGN PATENT DOCUMENTS

| | | |
|---|---|---|
| GB | 2070883 | 2/1981 |
| WO | WO 01/59480 | 8/2001 |

* cited by examiner

Primary Examiner—Craig E. Church
Assistant Examiner—Irakli Kiknadze
(74) Attorney, Agent, or Firm—Harness, Dickey & Pierce, PLC

(57) ABSTRACT

An apparatus for obtaining tomosynthesis data of an object (5) comprises a radiation source (1) emitting radiation (2) centered around an axis of symmetry (3); a radiation detector (6) comprising a stack of line detectors (6a), each being directed towards the divergent radiation source to allow a ray bundle (b1, . . . , $b_n$, . . . , $b_N$) of the radiation that propagates in a respective one of a plurality of different angles ($\alpha_1$, . . . , $\alpha_n$, . . . , $\alpha_N$) to enter the line detector; an object area arranged in the radiation path between the divergent radiation source and the radiation detector for housing the object; and a device (7) for moving the radiation source and the radiation detector relative the object essentially linearly in a direction (8) essentially orthogonal to the axis of symmetry, while each of the stack of line detectors is adapted to record a plurality of line images of radiation as transmitted through the object in a respective one of the plurality of different angles.

17 Claims, 2 Drawing Sheets

SCANNING-BASED DETECTION OF IONIZING RADIATION FOR TOMOSYNTHESIS

FIELD OF THE INVENTION

The invention relates generally to scanning-based apparatuses and methods for obtaining tomosynthesis data for examination of an object.

BACKGROUND OF THE INVENTION AND RELATED ART

An X-ray medical diagnostic method such as mammography is a low-dose procedure that creates one or more images of a part of a patient such as a breast thereof, which is to be examined, e.g. for detection of early stages of cancer.

The mammography diagnostic procedure generally includes obtaining two images of each of the patient's breasts, one from above and one from the side. A physician or radiologist then reviews the images of the breast, i.e., mammograms, to identify any breast cancer.

While this procedure is one of the best methods of detecting early forms of breast cancer, it is still possible for the detection of breast cancer to be missed by a physician or radiologist reviewing the mammograms. For example, breast cancer may be missed by being obscured by radiographically dense, fibroglandular breast tissue.

Tomosynthesis imaging, in which a plurality of images is acquired at different angles, has been studied in an effort to detect early forms of breast cancer. By shifting and adding the plurality of images, it is possible to reconstruct any plane in the breast being imaged that is parallel to the detector.

Further, various line detectors for detecting ionizing radiation are known in the art. While such detectors provide for instantaneous one-dimensional imaging, two-dimensional imaging can only be performed by means of scanning the line detector, and optionally the radiation source, in a direction traverse to the one-dimensional detector array. To use such a detector in tomosynthesis, wherein a plurality of images has to be acquired at different angles would be very time consuming.

SUMMARY OF THE INVENTION

A main object of the invention is therefore to provide a scanning-based apparatus and a method, respectively, for obtaining tomosynthesis data of an object at a higher speed than what is obtainable by using scanning-based apparatuses and methods of the prior art.

In this respect there is a particular object to provide such an apparatus and such a method, which are uncomplicated and can produce high-quality two-dimensional images with high spatial resolution, signal-to-noise ratio, dynamic range, and image contrast.

A yet further object of the invention is to provide such an apparatus and such a method, which are reliable, accurate, and inexpensive.

These objects, among others, are attained by apparatuses and methods as claimed in the appended claims.

The inventors have found that by providing a divergent radiation source emitting radiation centered around an axis of symmetry, and a radiation detector comprising a stack of line detectors, each being directed towards the divergent radiation source to allow a ray bundle of the radiation that propagates in a respective one of a plurality of different angles to enter the line detector after having been transmitted through an object to be examined, and moving the radiation source and the radiation detector relative the object linearly in a direction orthogonal to the axis of symmetry, while each of the line detectors records line images of radiation as transmitted through the object in a respective one of the different angles, a plurality of two-dimensional images can be formed, where each two-dimensional image is formed from a plurality of line images as recorded by a single one of the line detectors. Thus, a plurality of two-dimensional images at different angles are produced in a single scan, which reduces the detection time by a factor corresponding to the number of two-dimensional images produced. The data from the apparatus is excellent to be used in tomosynthesis or laminographic imaging.

The line detectors uses are preferably, but not exclusively, gaseous-based parallel plate detectors. Other line detectors that may be used include, scintillator-based arrays, CCD arrays, TFT- and CMOS-based detectors, liquid detectors, and diode arrays, e.g. PIN-diode arrays with edge-on, near edge-on or perpendicular incidence of X-rays.

Further characteristics of the invention, and advantages thereof, will be evident from the detailed description of preferred embodiments of the present invention given hereinafter and the accompanying FIGS. 1–2, which are given by way of illustration only, and thus are not limitative of the present invention.

DESCRIPTION OF PREFERRED EMBODIMENTS

Figure 1:
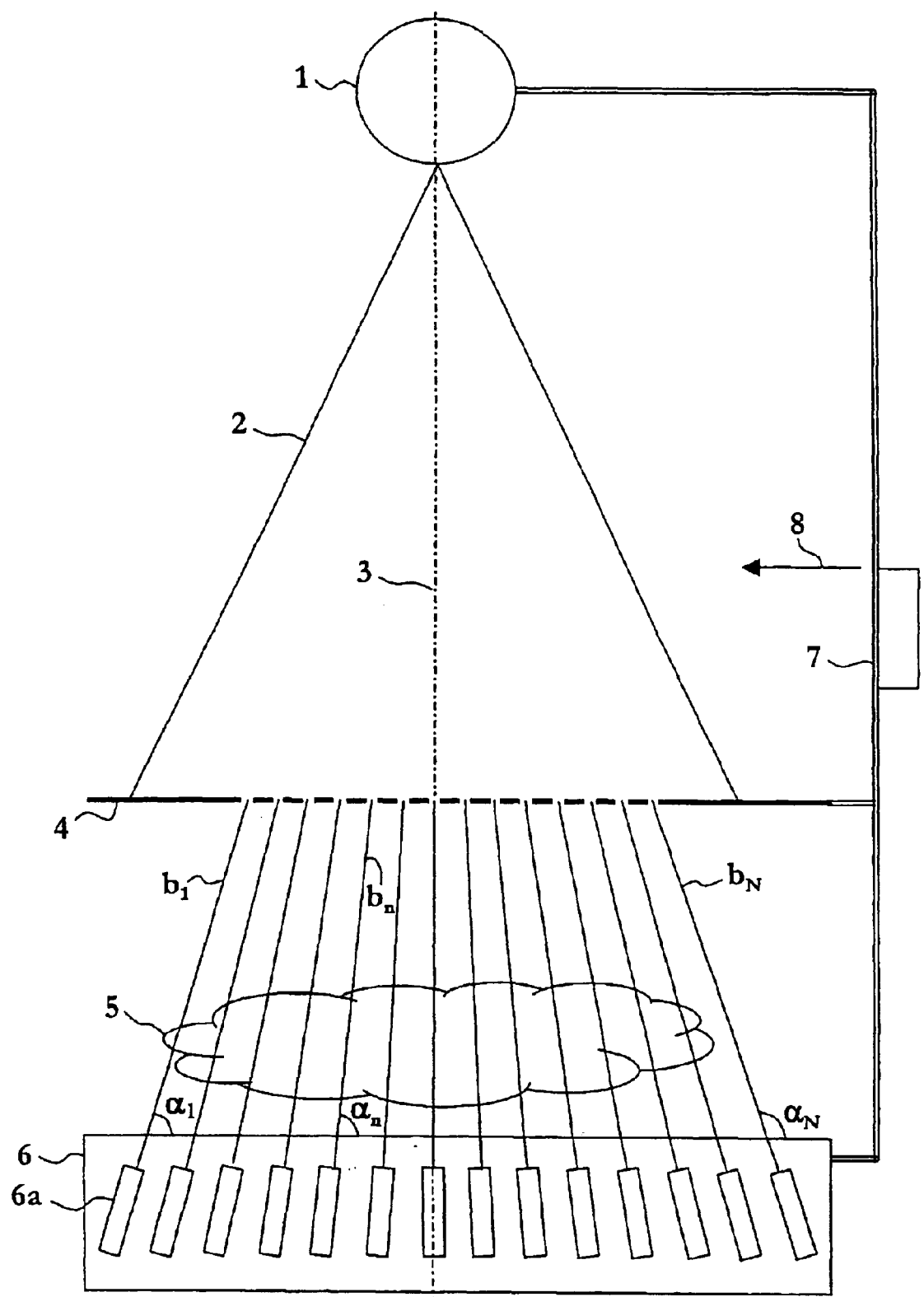
FIG. 1 illustrates schematically, in a top view, an apparatus for obtaining tomosynthesis data for x-ray examination of an object according to a preferred embodiment of the present invention.

The apparatus of FIG. 1 comprises a divergent X-ray source 1, which produces X-rays 2 centered around an axis of symmetry 3, a collimator 4, a radiation detector 6, and a device 7 for rigidly connecting the X-ray source 1, the collimator 4, and the radiation detector 6 to each other and moving the X-ray source 1, the collimator 4, and the radiation detector 6 linearly in direction 8 essentially orthogonal to the axis of symmetry 3 to scan scan an object 5, which is to be examined.

The radiation detector 6 comprises a stack of line detectors 6a, each being directed towards the divergent radiation source 1 to allow a respective ray bundle $b1, \ldots, b_n, \ldots, b_N$ of the radiation 2 that propagates in a respective one of a plurality of different angles $\alpha_1, \ldots, \alpha_n, \ldots, \alpha_N$ with respect to the front surface of the radiation detector 6 to enter the respective line detector 6a.

The collimator 4 may be a thin foil of e.g. tungsten with narrow radiation transparent slits etched away, the number of which corresponds to the number of line detectors 6a of the radiation detector 6. The slits are aligned with the line detectors 6a so that X-rays passing through the slits of the collimator 4 will reach the detector units 6a, i.e. as the respective ray bundles $b_1, \ldots, b_n, \ldots, b_N$. The collimator 4, which is optional, prevents radiation, which is not directed directly towards the line detectors 6a, from impinging on the object 5, thereby reducing the radiation dose to the object.

This is advantageous in all applications where the object is a human or an animal, or parts thereof.

During scanning the device 7 moves the radiation source 1 and the radiation detector 6 relative the object 5 in a linear manner parallel with the front of the radiation detector as being indicated by arrow 8, while each of the line detectors 6a records a plurality of line images of radiation as transmitted through the object 5 in a respective one of the different angles $\alpha_1, \ldots, \alpha_n, \ldots, \alpha_N$.

The scanning of the object 5 is performed a length, which is sufficiently large so that each one of the line detectors 6a can be scanned across the entire object of interest to obtain, for each of the line detectors 6a, a two-dimensional image of radiation as transmitted through the object 5 in a respective one of the different angles $\alpha_1, \ldots, \alpha_n, \ldots, \alpha_N$.

Figure 2A:
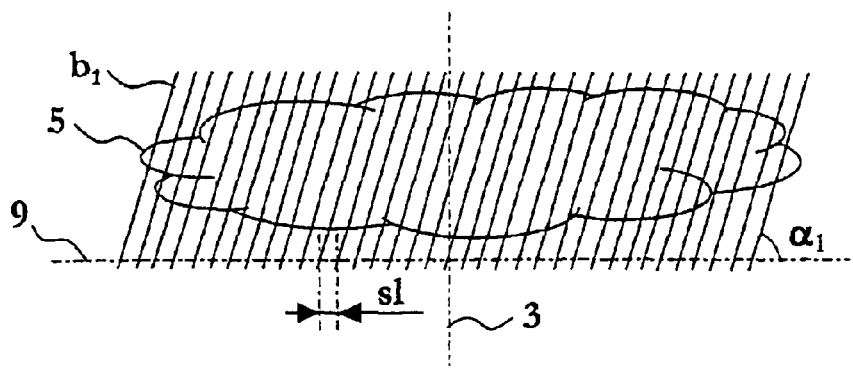
FIGS. 2a–c illustrate each schematically, in a top view, a particular X-ray bundle as it traverses the examination object during scanning by the apparatus of FIG. 1.
Figure 2B:
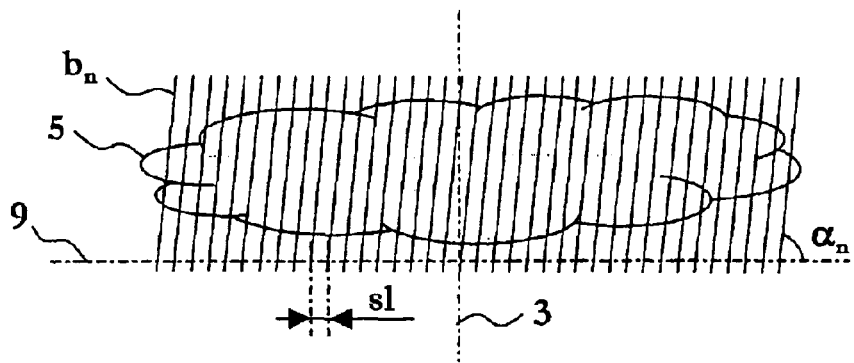
Figure 2C:
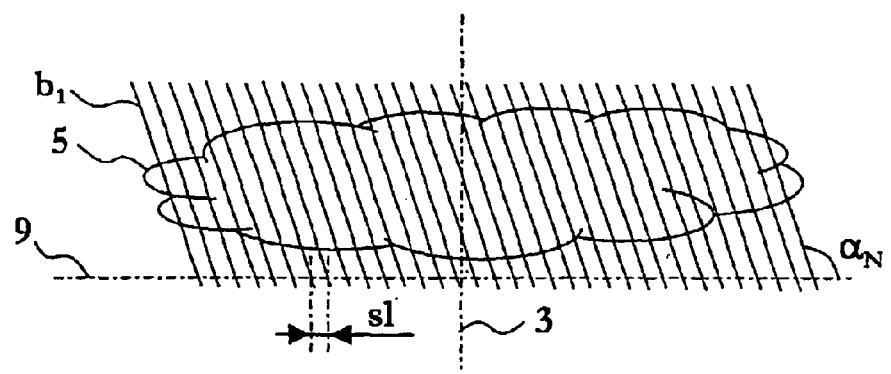

In FIGS. 2a–c three different X-ray bundles $b_1$, $b_n$, and $b_N$ are schematically illustrated as they traverse the examination object 5 during scanning by the apparatus of FIG. 1. Reference numeral 9 indicates a plane parallel with the scanning direction 8 and with the front of the radiation detector 2.

As can be seen in FIGS. 2a–c each line detector/x-ray bundle pair produces a complete two-dimensional image at a distinct one of the different angles. FIG. 2a illustrates the formation of a two-dimensional image of radiation transmitted through the object at an angle $\alpha_1$, FIG. 2b illustrates the formation of a two-dimensional image of radiation transmitted through the same object, but at an angle $\alpha_n$, and FIG. 2c illustrates the formation of a similar two-dimensional image, but at an angle $\alpha_N$.

Preferably, the different angles are distributed over an angular range $\alpha_N - \alpha_1$ of at least 5°, preferably at least 10°, and most preferably at least 15° depending on the application or kind of examination in order to obtain high-quality tomosynthesis data for examination of the object. The number of line detectors 6a in the stack of line detectors is at least 3, preferably at least 5, and most preferably at least 10 depending on the number of images recorded at different angles, which is required during the examination.

The scanning step, in FIGS. 2a–c denoted by s1, depends on the spatial resolution of the two-dimensional images formed from the one-dimensional recordings. Typically, the scanning step s1 can be about 100 microns, and the individual detecting elements of each of the line detectors can be of similar size.

It shall be noted that the present invention is applicable to any kind of examination employing tomosynthesis or laminographic imaging, including e.g. mammography examination and other soft tissue examinations.

A preferred line detector for use in the present invention is a gaseous-based parallel plate detector, preferably provided with an electron avalanche amplifier. Such a gaseous-based parallel plate detector is an ionization detector, wherein electrons freed as a result of ionization by ionizing radiation are accelerated in a direction essentially perpendicular to the direction of the radiation.

For further details regarding such kind of gaseous-based line detectors for use in the present invention, reference is made to the following U.S. Patents by Tom Francke et al. and assigned to XCounter AB of Sweden, which patents are hereby incorporated by reference: U.S. Pat. Nos. 6,546,070; 6,522,722; 6,518,578; 6,118,125; 6,373,065; 6,337,482; 6,385,282; 6,414,317; 6,476,397; and 6,477,223.

It shall particularly be pointed out that such kind of detector is very efficient in preventing Compton scattered radiation from being detected. This property is of outermost importance to obtain high-quality tomosynthesis data.

The distance between the parallel plates, i.e. electrodes, of the line detector may be below about 2 mm, preferably below about 1 mm, more preferably below about 0.5 mm, and most preferably between about 0.1 mm and 0.5 mm. XCounter AB has recently begun to verify the Compton scattering rejection characteristics of the line detector experimentally and good contrast has been observed using a wide X-ray spectrum of high energy X-rays, at which conditions a conventional detector system would not be capable to see any structure at all. It is believed that the above-depicted gaseous-based line detector discriminates more than 99% of the scattered photons; and by proper design it is assumed that about 99.9% or more of the scattered photons can be prevented from being detected.

It shall, nevertheless, be realized that any other may be used in the present invention. Such line detectors include scintillator-based arrays, CCD arrays, TFT- and CMOS-based detectors, liquid detectors, and solid-state detectors such as one-dimensional PIN-diode arrays with edge-on, near edge-on or perpendicular incidence of X-rays.

It shall further be appreciated that that the device 7 for rigidly connecting the X-ray source 1, the radiation detector 6, and the optional collimator 4 may be exchanged for separate devices (not illustrated) for the X-ray source 1, the radiation detector 6, and optionally the optional collimator 4, which may be controlled electronically to obtain synchronous linear movements of the separate devices to obtain the same scanning movement. Yet alternatively, the apparatus of FIG. 1 can be modified such the object 5 is moved during scanning, while the radiation source 1, the radiation detector 6, and the optional collimator 4 are kept at rest.

It shall still further be appreciated that the radiation detector 6 of the apparatus of FIG. 1 may be modified such that the line detectors, instead of being arranged in a linear stack, are arranged at the periphery of a circle, the center of which coinciding with the position of radiation source 1.

What is claimed is:

1. A scanning-based apparatus for obtaining tomosynthesis data of an object comprising:
   a divergent radiation source emitting radiation centered around an axis of symmetry;
   a radiation detector comprising a stack of line detectors, for creating tomosynthesis data, each line detector being directed towards the divergent radiation source to allow a ray bundle of said radiation that propagates in a respective one of a plurality of different angles to enter the line detector;
   an object area arranged in the radiation path between said divergent radiation source and said radiation detector for housing said object; and
   a device for moving said divergent radiation source and said radiation detector relative said object essentially linearly in a direction essentially orthogonal to said axis of symmetry, while each of said line detectors is adapted to record a plurality of line images of radiation as transmitted through said object in a respective one of said plurality of different angles.

2. The apparatus of claim 1 wherein said plurality of different angles are distributed over an angular range of at least 5°.

3. The apparatus of claim 1 wherein said plurality of different angles are distributed over an angular range of at least 10°.

4. The apparatus of claim 1 wherein said plurality of different angles are distributed over an angular range of at least 15°.

5. The apparatus of claim 1 wherein the number of line detectors in said stack of line detectors is at least 3.

6. The apparatus of claim 1 wherein the number of line detectors in said stack of line detectors is at least 5.

7. The apparatus of claim 1 wherein the number of line detectors in said stack of line detectors is at least 10.

8. The apparatus of claim 1 wherein said device for moving is adapted to move said divergent radiation source and said radiation detector relative said object a length which is sufficient for scanning each of said line detectors across the entire object to obtain, for each of said line detectors, a two-dimensional image of radiation as transmitted through said object in a respective one of said plurality of different angles.

9. The apparatus of claim 1 wherein said divergent radiation source is an x-ray source; and said line detectors are each a gaseous-based ionization detector, wherein electrons freed as a result of ionization by a respective ray bundle are accelerated in a direction essentially perpendicular to the direct of that ray bundle.

10. The apparatus of claim 9, wherein said gaseous-based ionization detector is an electron avalanche detector.

11. The apparatus of claim 1 wherein said line detectors are each any of a diode array, a scintillator-based array, a CCD array, a TFT- or CMOS-based detector, or a liquid detector.

12. The apparatus of claim 1 comprising a collimator arranged in the radiation path between said radiation source and said object area, said collimator preventing radiation, which is not directed towards said line detectors, from impinging on said object, thereby reducing the radiation dose to said object.

13. The apparatus of claim 1 comprising a collimator arranged in the radiation path between said radiation source and said object area, said collimator preventing radiation, which is not directed towards said line detectors, from impinging on said object, thereby reducing the radiation dose to said object, wherein said collimator comprises a plurality of slits, each being arranged to allow a respective one of the ray bundles to pass through.

14. The apparatus of claim 1 wherein the line detectors of said radiation detector are separated from each other.

15. The apparatus of claim 1 wherein each of the line detectors of said radiation detector is directed towards the divergent radiation source to allow a ray bundle of said radiation that propagates in a respective one of a plurality of different angles to enter the line detector, wherein the ray bundles are separated from each other when reaching the object area.

16. A scanning-based method for obtaining tomosynthesis data of an object using a divergent radiation source, which emits radiation centered around an axis of symmetry; and a radiation detector comprising a stack of line detectors, each being directed towards the divergent radiation source to allow a ray bundle of said radiation that propagates in a respective one of a plurality of different angles to enter the line detector, the scanning based method comprising the steps of:

arranging said object in the radiation path between said divergent radiation source and said radiation detector; and moving said divergent radiation source and said radiation detector relative said object essentially linearly in a direction essentially orthogonal to said axis of symmetry, while, by each of said line detectors, recording a plurality of line images of radiation as transmitted through said object in a respective one of said plurality of different angles for creating the tomosynthesis data.

17. The method of claim 16 wherein said divergent radiation source and said radiation detector are moved relative said object a length which is sufficient for scanning each of said line detectors across the entire object to obtain, for each of said line detectors, a two-dimensional image of radiation as transmitted through said object in a respective one of said plurality of different angles.

* * * * *